(12) United States Patent
Appling

(10) Patent No.: US 7,033,347 B2
(45) Date of Patent: Apr. 25, 2006

(54) ENDOVASCULAR LASER TREATMENT DEVICE

(75) Inventor: William M. Appling, Granville, NY (US)

(73) Assignee: AngioDynamics, Inc., New York, NY (US)

( * ) Notice: Subject to any disclaimer, the term of this patent is extended or adjusted under 35 U.S.C. 154(b) by 0 days.

(21) Appl. No.: 10/316,545

(22) Filed: Dec. 11, 2002

(65) Prior Publication Data
US 2004/0116912 A1    Jun. 17, 2004

(51) Int. Cl.
*A61B 18/18* (2006.01)

(52) U.S. Cl. .......................... 606/7; 606/15; 600/106; 600/117; 385/51; 385/60; 385/91

(58) Field of Classification Search .................. 606/7, 606/13–16; 600/106, 117; 607/88, 89; 385/15–94
See application file for complete search history.

(56) References Cited

U.S. PATENT DOCUMENTS

| | | | |
|---|---|---|---|
| 5,104,393 A | | 4/1992 | Isner et al. |
| 5,147,348 A | * | 9/1992 | Leckrone et al. ............. 606/16 |
| 5,152,277 A | | 10/1992 | Honda et al. |
| 5,152,761 A | * | 10/1992 | Muller et al. .................. 606/16 |
| 5,400,428 A | * | 3/1995 | Grace ........................ 385/115 |
| 5,569,240 A | | 10/1996 | Dowlatshahi et al. |
| 5,603,710 A | * | 2/1997 | Easley et al. .................. 606/15 |
| 5,620,438 A | | 4/1997 | Amplatz et al. |
| 5,725,514 A | * | 3/1998 | Grinblat et al. ............. 604/294 |
| 5,733,279 A | * | 3/1998 | Konwitz et al. ............... 606/15 |
| 5,827,313 A | | 10/1998 | Ream |
| 5,876,373 A | * | 3/1999 | Giba et al. ................ 604/95.04 |
| 5,993,072 A | * | 11/1999 | de Juan et al. ................ 385/78 |
| 6,019,756 A | | 2/2000 | Mueller et al. |
| 6,126,653 A | | 10/2000 | Hajjar |
| 6,126,654 A | * | 10/2000 | Giba et al. ..................... 606/15 |
| 6,168,591 B1 | | 1/2001 | Sinofsky |
| 6,200,332 B1 | | 3/2001 | Del Giglio |
| 6,572,608 B1 | * | 6/2003 | Lee et al. ..................... 606/15 |
| 6,585,727 B1 | * | 7/2003 | Cashman et al. ............. 606/16 |
| 6,692,486 B1 | * | 2/2004 | Jaafar et al. .................. 606/7 |
| 6,817,973 B1 | * | 11/2004 | Merril et al. ............... 600/118 |

FOREIGN PATENT DOCUMENTS

| | | |
|---|---|---|
| EP | 0904797 A2 | 3/1999 |
| WO | WO 02/102266 | 12/2002 |

* cited by examiner

*Primary Examiner*—A. Farah
(74) *Attorney, Agent, or Firm*—Harry K. Ahn; Reed Smith, LLP

(57) ABSTRACT

An endovascular laser treatment device preferably includes a catheter having a hub at its proximal end, an optical fiber for insertion into the catheter, a fiber connector attached to the optical fiber at a selected distance from the distal end of the optical fiber, and a temporary stop removably mounted around the optical fiber. The treatment device has two positions: a protective position and an operating position. As the fiber is inserted through the catheter, the temporary stop rests against the hub and places the fiber tip in the protective position where the distal end of the optical fiber is positioned near the distal end of the catheter, but is still disposed inside the catheter. When the temporary stop is removed and the fiber connector is coupled with the catheter hub, the fiber tip is in the operating position where the distal end of the optical fiber extends past the distal end of the catheter by a predetermined distance to expose the fiber tip.

19 Claims, 3 Drawing Sheets

ENDOVASCULAR LASER TREATMENT DEVICE

FIELD OF THE INVENTION

The present invention relates to a medical device apparatus for treatment of venous disease, and more particularly, to a device for treating varicose veins using an endovascular laser fiber and catheter.

BACKGROUND OF THE INVENTION

Veins are thin-walled and contain one-way valves that control blood flow. Normally, the valves open to allow blood to flow into the deeper veins and close to prevent back-flow into the superficial veins. When the valves are malfunctioning or only partially functioning, however, they no longer prevent the back-flow of blood into the superficial veins. As a result, venous pressure builds at the site of the faulty valves. Because the veins are thin walled and not able to withstand the increased pressure, they become what are known as varicose veins which are veins that are dilated, tortuous or engorged.

In particular, varicose veins of the lower extremities is one of the most common medical conditions of the adult population. It is estimated that varicose veins affect approximately 25% of adult females and 10% of males. Symptoms include discomfort, aching of the legs, itching, cosmetic deformities, and swelling. If left untreated, varicose veins may cause medical complications such as bleeding, phlebitis, ulcerations, thrombi and lipodermatosclerosis.

Traditional treatments for varicosities include both temporary and permanent techniques. Temporary treatments involve use of compression stockings and elevation of the diseased extremities. While providing temporary relief of symptoms, these techniques do not correct the underlying cause, that is the faulty valves. Permanent treatments include surgical excision of the diseased segments, ambulatory phlebectomy, and occlusion of the vein through chemical or thermal means.

Surgical excision requires general anesthesia and a long recovery period. Even with its high clinical success rate, surgical excision is rapidly becoming an outmoded technique due to the high costs of treatment and complication risks from surgery. Ambulatory phlebectomy involves avulsion of the varicose vein segment using multiple stab incisions through the skin. The procedure is done on an outpatient basis, but is still relatively expensive due to the length of time required to perform the procedure.

Chemical occlusion, also known as sclerotherapy, is an in-office procedure involving the injection of an irritant chemical into the vein. The chemical acts upon the inner lining of the vein walls causing them to occlude and block blood flow. Although a popular treatment option, complications can be severe including skin ulceration, anaphylactic reactions and permanent skin staining. Treatment is limited to veins of a particular size range. In addition, there is a relatively high recurrence rate due to vessel recanalization.

Endovascular laser therapy is a relatively new treatment technique for venous reflux diseases. In that technique, the laser energy is delivered by a flexible optical fiber that is percutaneously inserted into the diseased vein prior to energy delivery. An introducer catheter or sheath is first inserted and advanced to within a few centimeters of the saphenous-femoral junction of the greater saphenous vein. Once the introducer catheter is properly positioned, a flexible optical fiber is inserted into the lumen of the catheter or sheath and advanced until the fiber tip is near the catheter tip but still protected within the catheter lumen.

For proper positioning, a medical tape is conventionally used to pre-measure and mark the optical fiber before insertion into the catheter. The physician measures the catheter length and then marks the fiber with the tape at a point approximately 1–3 centimeters longer than the overall catheter length. This measurement is used to establish correct placement of the fiber tip relative to the catheter in an exposed position.

Prior to laser activation, the catheter is withdrawn approximately 1–3 centimeters (position being indicated by a tape mark or the like) to expose the distal tip of the optical fiber. The laser generator is then activated causing laser energy to be emitted from the bare flat tip of the fiber into the vessel. The energy contacts the blood causing hot bubbles of gas to be created. The gas bubbles transfer thermal energy to the vein wall, causing cell necrosis and eventual vein collapse. With the laser generator turned on, the fiber and catheter are slowly withdrawn as a single unit until the entire diseased segment of the vessel has been treated.

For such endovascular laser treatment, the position of the fiber tip relative to the catheter is considered to be a very important parameter. Current laser treatment protocols recommend exposing the fiber tip by holding the fiber element stationary while withdrawing the catheter approximately 1 to 3 centimeters. Location of the fiber tip is then confirmed using ultrasound guidance and direct visualization of the red aiming beam of the fiber. Once correct positioning has been verified, the optical fiber is secured to the introducer catheter, typically with medical grade adhesive tape to ensure that the fiber and the catheter do not move independently of each other during the laser procedure.

As can be appreciated, there are many problems associated with using a medical tape for fiber positioning prior to insertion into the catheter or for joining the fiber and catheter together. It is cumbersome, inaccurate and time-consuming for the treating physician. Moreover, using the tape for positioning may cause damage to the fiber as the physician must straighten out the fiber for measurement. The tape may also be incorrectly located on the fiber. When using the tape to join the fiber and catheter together, it is possible that the tape does not adequately hold them in a stationary position, resulting in improper alignment of the fiber with respect to the catheter.

Complications caused by mishandling and improper positioning of the optical fiber can be severe. Mishandling can result in fiber breakage or incomplete energy delivery. Improper positioning of the fiber relative to the catheter cause other problems. If the fiber tip is too close to the catheter tip, the catheter material may be thermally heated by the laser energy to the extent that the catheter tip integrity is compromised. If the fiber tip extends too far from the catheter tip, the exposed portion of the fiber tip may become damaged or cause energy to be delivered to a non-target area during withdrawal. For example, the physician may begin laser treatment at a point in the venous system that is too deep, resulting in possible deep vein thrombosis. Improper positioning of the tip may also cause the physician to stop treatment prematurely resulting in a non-occluded vessel segment.

Therefore, it is desirable to provide a reliable endovascular laser treatment device that safely stops the optical fiber in a protective position during insertion and safely secures the fiber in an operating position without using a medical tape and without requiring the user to pre-measure the optical fiber.

It is also desirable to provide such an endovascular laser treatment device that can be manufactured at a low cost and that can reduce the fiber insertion time.

SUMMARY OF THE DISCLOSURE

According to the principles of the present invention, an endovascular laser treatment device is provided. In one embodiment, the device includes a catheter having a hub at its proximal end, an optical fiber for insertion into the catheter, and a permanent stop attached to the optical fiber at a selected distance from the distal end of the optical fiber. The permanent stop may be a fiber connector that can be mated or coupled with the hub.

The catheter is initially inserted into a blood vessel. When the catheter is positioned inside the blood vessel, the optical fiber is inserted through the catheter. The fiber connector, which is attached to the optical fiber, is then coupled with the hub. When the fiber connector is in contact with or coupled with the hub, the distal end of the optical fiber extends past the distal end of the catheter by a predetermined distance to place the fiber tip in an operating position.

In another aspect of the invention, a temporary stop is removably mounted around the optical fiber distal of the permanent stop. The temporary stop is longitudinally slidable on the optical fiber. As the fiber is inserted through the catheter and before the device is put into the operating position, the temporary stop contacts and rests against the catheter hub. At this point, the optical fiber is in a protective position where the distal end of the optical fiber is positioned near the distal end of the catheter, but is still disposed inside the catheter. The temporary fiber stop provides the necessary shielding of the fiber tip to ensure that the protective fiber position is maintained during any required adjustments prior to placing the optical fiber in the operating position. The temporary stop is designed to be pulled off manually from the optical fiber or to automatically disengage when the catheter is retracted to expose the fiber in the operating position.

DETAILED DESCRIPTION OF THE INVENTION

Figure 1:
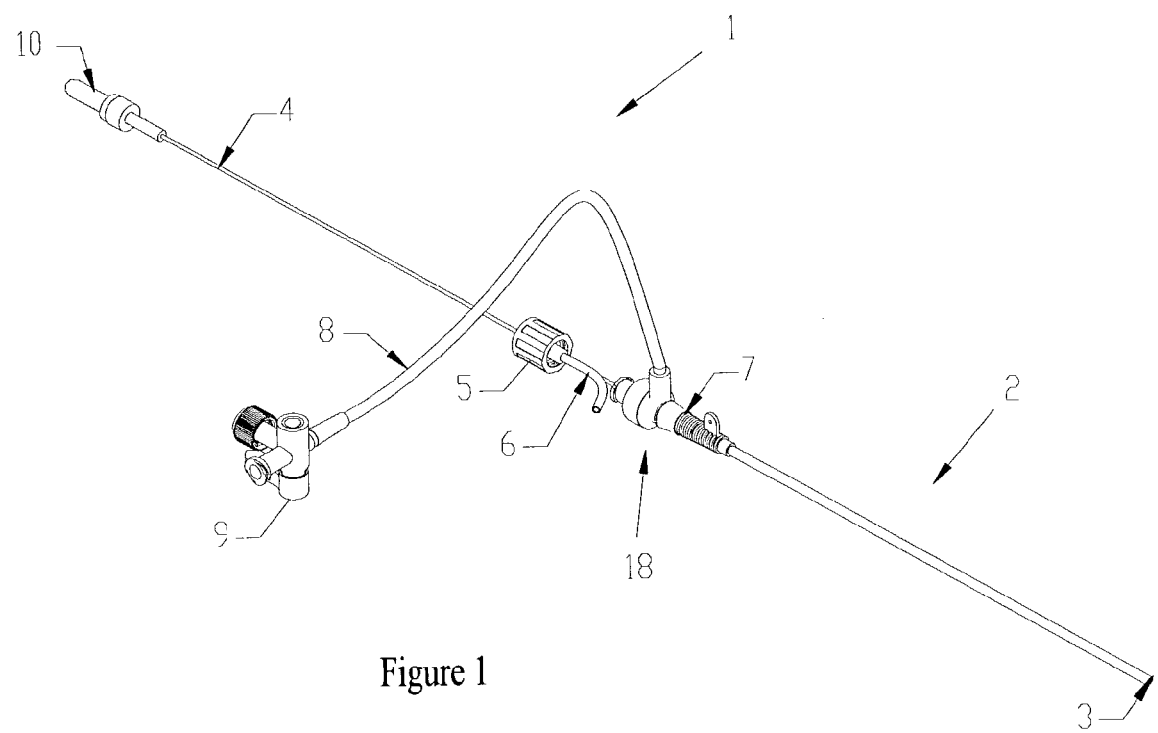
FIG. 1 illustrates an endovascular laser treatment device with a fiber tip in a protective position within a catheter according to the invention.

An endovascular laser treatment device 1 according to the present invention is illustrated in FIG. 1. The laser treatment device 1 includes a catheter assembly 2 having a hub 18, an optical fiber 4, a permanent fiber stop 5 in the form of a fiber connector attached to the optical fiber and a temporary fiber stop 6.

Figure 4:
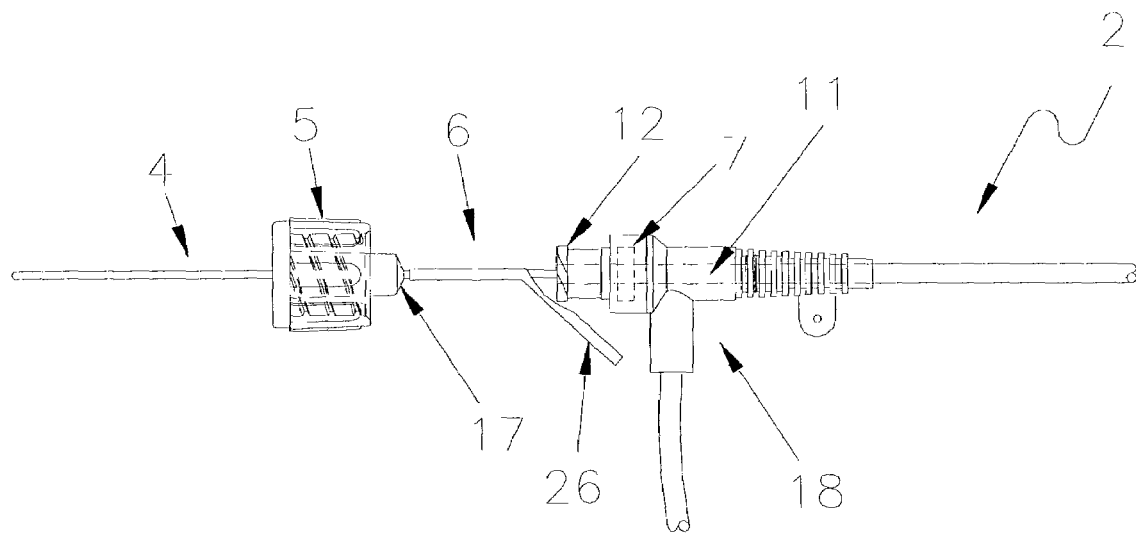
FIG. 4 illustrates various components of the endovascular laser treatment device of FIG. 1 with the optical fiber in the protective position.

The catheter 2 is a tubular structure used to facilitate the passage of the optical fiber 4 within the cardiovascular system of a patient. As shown in FIG. 4, the catheter 2 has a catheter tip 3 (shown in FIG. 1) with a through-lumen 11 for insertion and passage of the optical fiber 4. The catheter 2 has a hub 18 having a hub connector 12 which is designed to mate and lock with the fiber connector 5 attached to the optical fiber 4. As used herein, the catheter 2 can be a sheath, dilator or any other tubular device designed to aid in insertion and advancement of the optical fiber 4 through a blood vessel.

In a preferred embodiment, the catheter 2 is comprised of a hemostasis valve 7, side arm tubing 8 and a stopcock 9. The hemostasis valve 7 is a passive one-way valve that prevents the backflow of blood from the through-lumen 11 of the catheter 2 while simultaneously allowing the introduction of fibers, guidewires and other interventional devices into the catheter. The passive valve 7 is located within the lumen 11 of the catheter hub 18. The valve 7 is made of elastomeric material such as a rubber or latex, as commonly found in the art. The valve 7 opens to allow insertion of the fiber 4 and then seals around the inserted fiber. However, the valve 7 does not open in response to pressure from the distal side in order to prevent the backflow of blood or other fluids. The valve 7 also prevents air from entering the catheter 2 through the hub connector 12.

A stopcock 9 and side arm tubing 8 provide multiple fluid paths for administering optional procedural fluids during a treatment session. As shown in FIG. 1, the stopcock 9 may be a three-way valve with a small handle (not shown) that can be moved to alter the fluid path. The position of the handle controls the active fluid path by shutting off the flow from one or both ports of the stopcock 9. Fluid flow is directed through the side arm tubing 8 into or out of the catheter 2.

One commonly administered fluid during an endovascular laser treatment procedure is saline which is used to flush blood from the catheter 2 prior to insertion of the optical fiber 4. Blood is often flushed from the catheter 2 to prevent the adherence of blood to the fiber tip 13 (FIG. 2), which can adversely affect the intensity and direction of the laser energy within the vessel. The stopcock 9 can also be used to administer emergency drugs directly into the vein or to confirm device position within the vein by the visual backflow of blood into the side arm 8.

Figure 3:
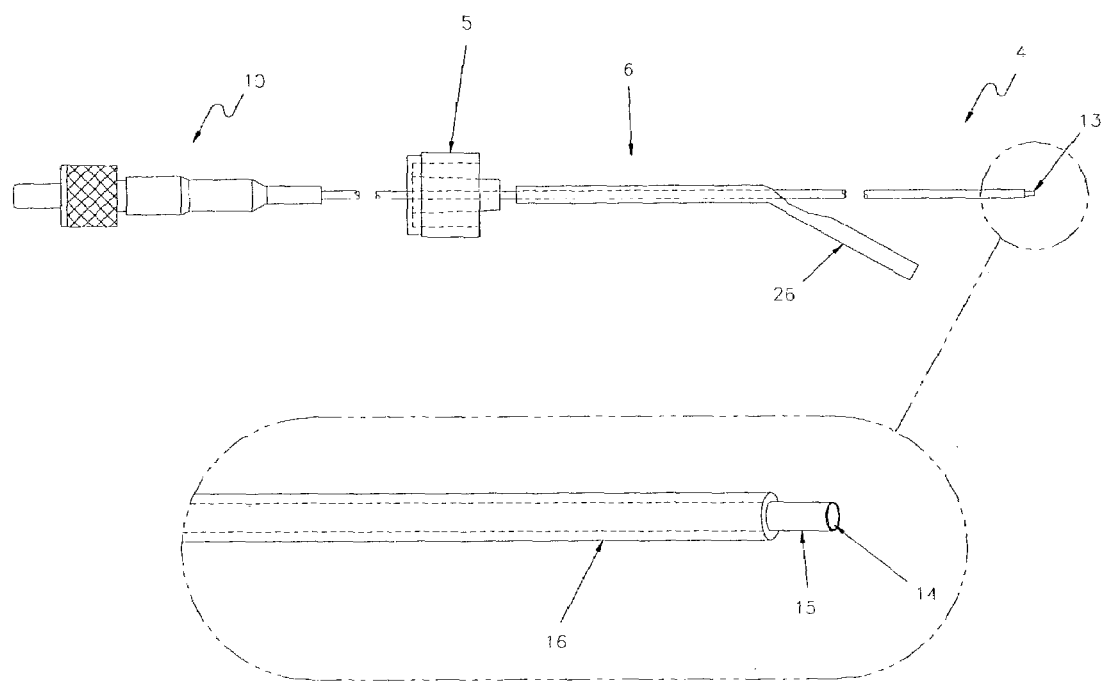
FIG. 3 illustrates various components, including a permanent fiber stop and a temporary fiber stop, of the endovascular laser treatment device of FIG. 1 with an enlarged view of the optical fiber.

The optical fiber 4, depicted in detail in FIG. 3, is a standard laser fiber composed of a thin filament of glass 14 or similar material surrounded by a silica cladding 15. A plastic, coaxially mounted protective jacket 16 surrounds the fiber cladding 15 to provide additional strength, protection from surface damage and isolation from moisture. The protective jacket 16 terminates approximately 4 mm from the distal tip 13 of the fiber 4. The optical fiber 4 is typically between 400 and 1000 microns in diameter, preferably 600 microns. The end of the fiber 4 terminates at the energy-emitting end, which is the flat-faced surface of the fiber tip 13. At the proximal end, the fiber 4 is connected to a connector 10 such as a standard SMA connector. The connector 10 connects the fiber 4 to a laser source (not shown).

According to the present invention, the fiber connector 5 and the temporary stop 6 are used to position the fiber during its insertion through the catheter 2 and to fix the fiber to the catheter during the vein treatment procedure.

The fiber connector 5 is permanently bonded to the fiber 4 at a predetermined distance from the fiber tip 13. In a preferred embodiment, the fiber connector 5 is a standard male Luer connector having a through-hole through which the fiber 4 passes and through which the fiber is glued.

Figure 2:
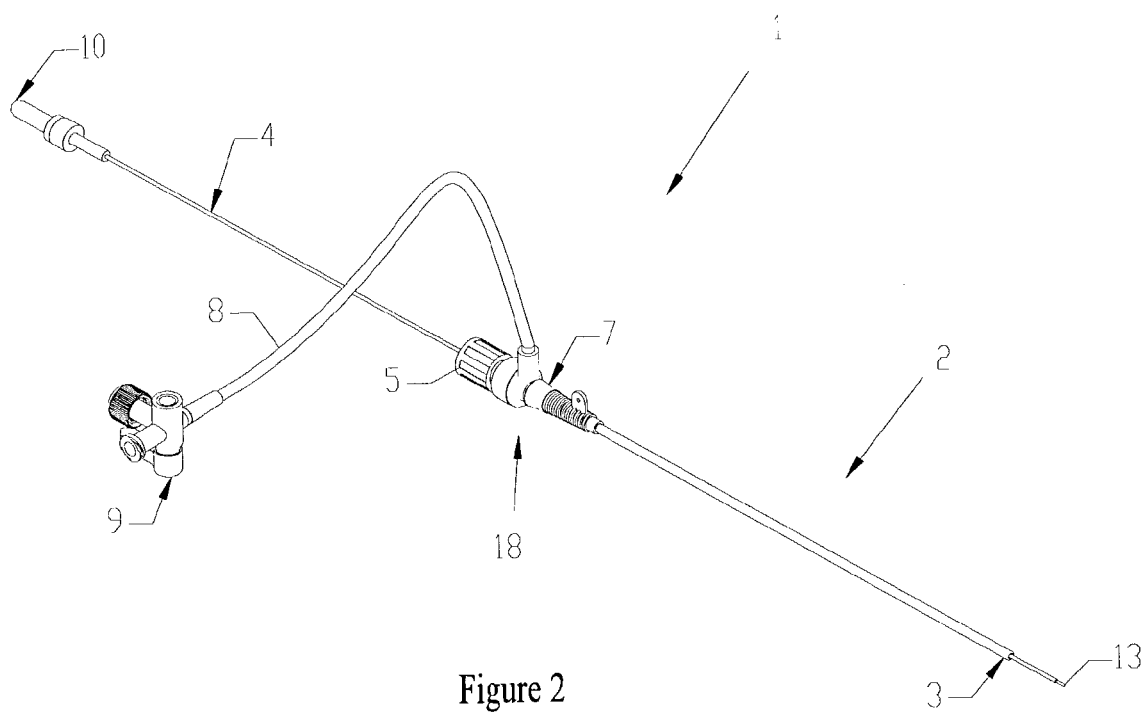
FIG. 2 illustrates the endovascular laser treatment device of FIG. 1 with the fiber tip in an exposed or operating position.

The male Luer connector 5 is designed to lock with a female Luer connector (hub connector) 12 disposed at the hub 18. When the fiber 4 is inserted through the catheter 2 and the fiber connector 5 is locked with the hub connector 12, the laser treatment device 1 is in a locked operating position as shown in FIG. 2. In that operating position, the fiber tip 13 extends past the catheter tip 3 by a set amount, for example by between 1 and 3 centimeters, to expose the fiber tip 13. Advantageously, the locking mechanism of the connectors 5, 12 secures the fiber 4 to the catheter so that there can be no independent movement of the fiber 4 relative to the catheter 2. Use of medical tape or the like is not required. Also, because the fiber connector 5 is bonded to the fiber 4 at a precise distance away from the fiber tip 13, the physician can be assured that the fiber tip 13 is positioned precisely relative to the catheter tip 3 without being concerned about fiber misalignment that often occurred previously using a conventional medical tape.

Figure 5A:
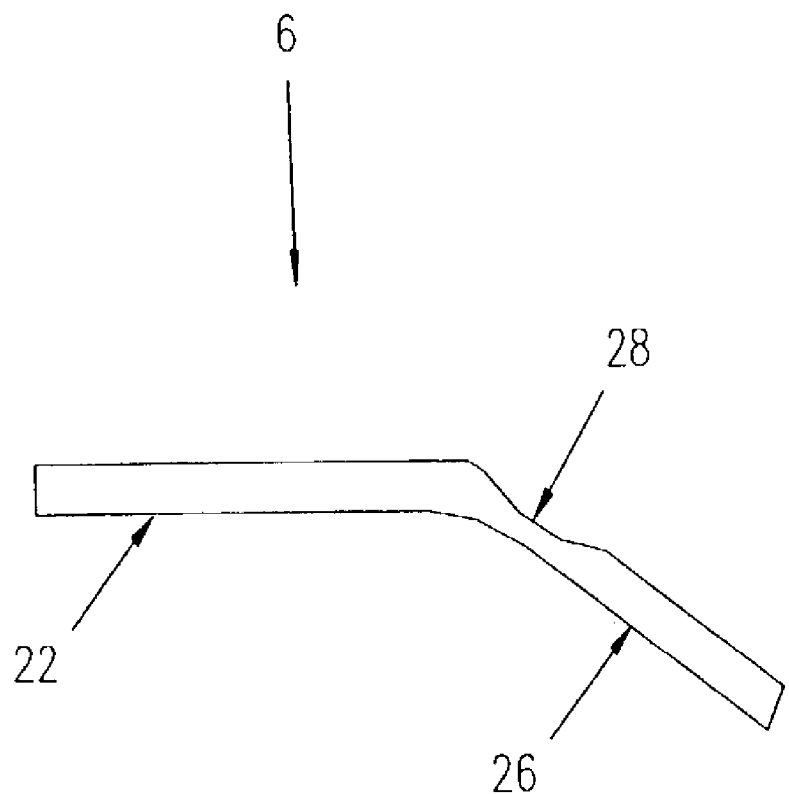
FIG. 5(A) is an enlarged plan view of a temporary fiber stop component for the endovascular laser treatment device of FIG. 1.
Figure 5B:
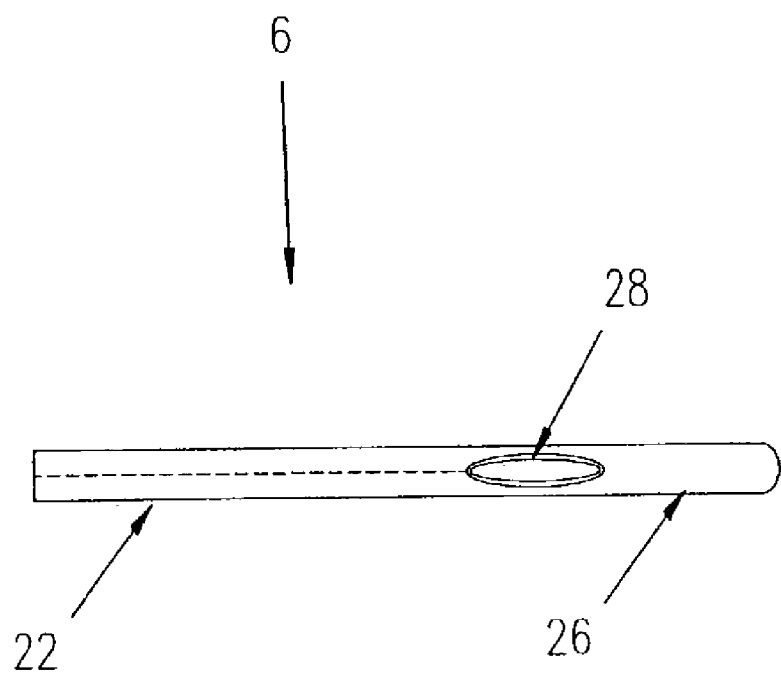
FIG. 5(B) is an enlarged side view of the temporary fiber stop component for the endovascular laser treatment device of FIG. 1.

Before the connectors 5, 12 are locked with each other, the temporary stop 6 is used to pre-position the fiber 4 in a protected position within the catheter 2 to insure that the fiber 4 does not inadvertently advance beyond the catheter tip 3 during insertion and positioning of the catheter 2. As shown in FIGS. 4, and 5(A) and 5(B), the temporary stop is a tubular element comprised of a longitudinal segment 22 and an angled segment 26.

The longitudinal segment 22 is a cylindrical body portion having a longitudinal slit 20. The angled segment 26 has a recess portion 28 and is integrally attached to the longitudinal segment 22 at an angle. Preferably, the inner diameter of the longitudinal segment 22 is dimensioned such that it receives the fiber 4 with sufficient annular space to allow free sliding movement of the temporary stop 6 along the axis of the optical fiber 4, as shown in FIG. 3.

As the fiber 4 is inserted through the catheter 2, the hub connector 12 comes in contact with and rests against the angled segment 26 at the recess 28 while the proximal end of the longitudinal segment 22 contacts the fiber connector 5. That is, the hub connector 12 rests against the recess 28. At this point, the fiber 4 is in the protected position and the recess 28 prevents the fiber from advancing further into the catheter 2. In the protected position, the fiber tip 13 is near the catheter tip 3, but is still protected within the catheter 2. The longitudinal segment 22 and the recess 28 are dimensioned to ensure that in the protected position, the fiber tip 13 is not exposed outside of the catheter 2. Advantageously, the temporary fiber stop 6 provides the physician with a tactile acknowledgement and a visible marker that the optical fiber 4 is now in the protected position.

The optical fiber 4 is now ready to be placed in the operating position. The longitudinal slit 20 along with the angled segment 26, which acts as a handle, allows the physician to easily remove the temporary stop 6 in order to lock the fiber connector 5 with the hub connector 12. Preferably, the temporary stop 6 is removed by grabbing the angled segment 26 and gently pulling it away from the fiber 4. Alternatively, the temporary stop 6 can be removed by holding the fiber 4 stationary and gently retracting the catheter causing the temporary stop 6 to pop off the optical fiber 4. In that case, the angled segment 26 including the recess 28 acts as a ramp to apply an angular force against the optical fiber 4 to open the longitudinal slit 20.

A preferred method of using the endovascular laser device 1 in treating varicose veins will now be described. The treatment procedure begins with the standard pre-operative preparation of the patient as is well-known in the laser treatment art. Prior to the laser treatment, the patient's diseased venous segments are marked on the skin surface. Typically, ultrasound guidance is used to map the greater saphenous vein from the sapheno-femoral junction to the popliteal area.

The greater saphenous vein is accessed using a standard Seldinger technique. A guide wire is advanced into the vein, and then the catheter 2 is fed over the guidewire and advanced to 1 to 2 centimeters below the sapheno-femoral junction. Position of the catheter 2 is then verified and adjusted if necessary using ultrasound. Once correct positioning is confirmed, the guide wire is removed leaving the catheter 2 in place.

The distal tip 13 of the optical fiber 4 is then inserted into the catheter hub 18 and advanced until the temporary stop 6 is positioned between the hub connector 12 and the fiber connector 5 in the protective position as discussed above. As shown in FIG. 1, the fiber tip 13 is correctly aligned in the protective position within the catheter 2 lumen when the hub connector 12 rests against the recess 28 of the angled segment 26 and the proximal end of the longitudinal segment 22 is in contact with the fiber connector 5. Once again, correct positioning of the catheter 2 and fiber tip 13 approximately 1–2 centimeters below the Sapheno-femoral junction is confirmed using ultrasound. At this point, any required adjustments can be made to the overall device position. The temporary fiber stop 6 provides the necessary spacing between the catheter tip 3 and fiber tip 13 to ensure that the protective fiber position is maintained during any required adjustments.

In preparation for laser activation, the temporary stop 6 is removed by either pulling on the angled segment 26 or retracting the catheter until the hub contacts the the fiber connector 5 at the recess 28 causing it to pop off. As discussed above, the longitudinal slit 20 on the temporary fiber stop 6 facilitates easy removal from the optical fiber 4. Once the temporary fiber stop 6 has been removed, the physician pulls the hub 18 back while holding the fiber 4 stationary and then locks the hub connector 12 with the fiber connector 5. Once locked together, the tip 13 of the fiber 4 extends beyond the catheter tip 3 by, for example, approximately 2 centimeters as shown in FIG. 2.

The device 1 is now in the operating position, ready to delivery laser energy to the diseased vein. The laser generator (not shown) is activated and the catheter 2/ fiber 4 assembly is slowly withdrawn together through the vein, preferably at a rate of 1–3 millimeters per second. The connection between the fiber connector 5 and the hub connector 12 ensures that the fiber tip 4 remains exposed beyond the catheter tip 3 by the recommended length for the entire duration of the treatment procedure.

The procedure for treating the varicose vein is considered to be complete when the desired length of the greater saphenous vein has been exposed to laser energy. Normally, the laser generator is turned off when the fiber tip 13 is approximately 3 centimeters from the access site. The fiber 4/catheter 2 assembly is then removed from the body as a single unit.

While certain novel features of this invention have been shown and described above, the present invention may be embodied in other specific forms without departing from the spirit or essential characteristics of the invention. The described embodiments are to be considered in all respects only as illustrative and not as restrictive. Various omissions, modifications, substitutions and changes in the forms and details of the device illustrated and in its operation can be made by those skilled in the art without departing in any way from the spirit of the present invention.

What is claimed is:

1. An endovascular laser treatment device, comprising:
  a catheter having a hub at its proximal end and being operable to be inserted into a blood vessel;
  an optical fiber for insertion into the catheter; and
  a permanent stop immovably and non-adjustably attached to the optical fiber at a selected distance from the distal end of the optical fiber such that when the optical fiber is inserted through the catheter and the permanent stop is in contact with the hub, the distal end of the optical fiber extends past the distal end of the catheter by a predetermined distance.

2. The endovascular laser treatment device according to claim 1, further comprising a temporary stop removably disposed near the optical fiber and distal of the permanent stop such that when the temporary stop is in contact with the hub and the permanent stop as the optical fiber is inserted into the catheter, the optical fiber is in a protective position where the distal end of the optical fiber is positioned near the distal end of the catheter and inside the catheter.

3. The endovascular laser treatment device according to claim 2, wherein the temporary stop comprises:
  a longitudinal segment having a longitudinal slit and being mounted around the optical fiber; and
  an angled segment attached to the longitudinal segment at an angle.

4. The endovascular laser treatment device according to claim 3, wherein in the protective position, the hub rests against the angled segment.

5. The endovascular laser treatment device according to claim 1, further comprising a hub connector attached to the hub wherein the permanent stop is a fiber connector capable of being mated with the hub connector.

6. The endovascular laser treatment device according to claim 5, wherein the fiber connector has a through hole through which the optical fiber passes and the fiber connector is bonded to the fiber connector at the through-hole.

7. An endovascular laser treatment device, comprising:
  a catheter having a hub at its proximal end and being operable to be inserted into a blood vessel;
  an optical fiber for insertion into the catheter positioned inside the blood vessel;
  a permanent stop attached to the optical fiber at a selected distance from the distal end of the optical fiber such that when the optical fiber is inserted through the catheter and the permanent stop is in contact with the hub, the distal end of the optical fiber extends past the distal end of the catheter by a predetermined distance; and
  a temporary stop removably disposed around the optical fiber and distal of the permanent stop such that when the temporary stop is in contact with both the hub and the permanent stop as the optical fiber is inserted into the catheter, the optical fiber is in a protective position where the distal end of the optical fiber is positioned near the distal end of the catheter and inside the catheter.

8. An endovascular laser treatment device, comprising:
  a catheter having a hub at its proximal end and being operable to be inserted into a blood vessel;
  an optical fiber for insertion into the catheter; and
  a fiber connector immovably and non-adjustably attached to the optical fiber at a selected distance from the distal end of the optical fiber such that when the optical fiber is inserted through the catheter and the fiber connector is coupled to the hub, the distal end of the optical fiber extends past the distal end of the catheter by a predetermined distance.

9. The endovascular laser treatment device according to claim 8, further comprising a temporary stop removably disposed near the optical fiber between the fiber connector and the hub such that when the temporary stop contacts both the hub and the fiber connector as the optical fiber is inserted into the catheter, the optical fiber is in a protective position where the distal end of the optical fiber is positioned near the distal end of the catheter and inside the catheter.

10. The endovascular laser treatment device according to claim 9, wherein the temporary stop comprises:
  a longitudinal segment having a longitudinal slit; and
  an angled segment attached to the longitudinal segment at an angle.

11. The endovascular laser treatment device according to claim 10, wherein the longitudinal segment includes a cylindrical tube mounted around the optical fiber.

12. The endovascular laser treatment device according to claim 10, wherein the angled segment includes a recess portion that contacts the hub when the optical fiber is in the protective position.

13. The endovascular laser treatment device according to claim 10, wherein when the optical fiber is in the protective position and the catheter is moved toward the fiber connector, the temporary stop detaches from the optical fiber.

14. The endovascular laser treatment device according to claim 10, wherein when the optical fiber is in the protective position, the temporary stop is removable by pulling the angled segment away from the optical fiber.

15. The endovascular laser treatment device according to claim 8, wherein:
  the fiber connector is a male connector; and
  the hub includes a female connector that is mated with the male connector.

16. The endovascular laser treatment device according to claim 8, wherein the fiber connector has a through-hole through which the optical fiber passes.

17. The endovascular laser treatment device according to claim 8, wherein the hub includes a port in communication with the catheter for connecting a side tube.

18. An endovascular laser treatment device, comprising:
  a catheter operable to be inserted into a blood vessel;
  a catheter connector attached to the proximal end of the catheter;
  an optical fiber for insertion into the catheter; and
  a fiber connector immovably and non-adjustably attached to the optical fiber at a selected distance from the distal end of the optical fiber wherein when the optical fiber is inserted through the catheter and the fiber connector is coupled with the catheter connector, the distal end of the optical fiber extends past the distal end of the catheter by a predetermined distance.

19. A laser treatment device for use in endovascular treatment, comprising:
a catheter operable to be inserted into a blood vessel;
a hub having a hub connector and attached to the proximal end of the catheter;
an optical fiber for insertion into the catheter; and
a fiber connector attached to the optical fiber at a selected distance from the distal end of the optical fiber such that when the optical fiber is inserted through the catheter and the fiber connector is coupled with the hub connector, the distal end of the optical fiber extends past the distal end of the catheter by a predetermined distance to place the optical fiber in an operating position; and
a temporary stop removably disposed between the fiber connector and the hub connector during insertion of the fiber into the catheter to place the optical fiber in a protective position where the distal end of the optical fiber is positioned near the distal end of the catheter and inside the catheter.

* * * * *